(12) United States Patent
De Gunzburg et al.

(10) Patent No.: US 11,365,403 B2
(45) Date of Patent: Jun. 21, 2022

(54) BETA-LACTAMASE VARIANTS

(71) Applicants: Da Volterra, Paris (FR); Bioaster, Lyons (FR)

(72) Inventors: Jean De Gunzburg, London (GB); Jean-Denis Docquier, Sovicille (IT)

(73) Assignees: Da Volterra, Paris (FR); Bioaster, Lyons (FR)

( * ) Notice: Subject to any disclaimer, the term of this patent is extended or adjusted under 35 U.S.C. 154(b) by 11 days.

(21) Appl. No.: 16/757,968

(22) PCT Filed: Oct. 24, 2018

(86) PCT No.: PCT/EP2018/079223
§ 371 (c)(1),
(2) Date: Apr. 21, 2020

(87) PCT Pub. No.: WO2019/081614
PCT Pub. Date: May 2, 2019

(65) Prior Publication Data
US 2020/0318094 A1    Oct. 8, 2020

(30) Foreign Application Priority Data
Oct. 25, 2017 (EP) ..................... 17198414

(51) Int. Cl.
| | |
|---|---|
| *C12N 9/84* | (2006.01) |
| *C12N 1/21* | (2006.01) |
| *A61K 38/50* | (2006.01) |
| *C12N 9/86* | (2006.01) |
| *A61K 31/407* | (2006.01) |
| *A61K 31/496* | (2006.01) |
| *A61K 31/546* | (2006.01) |
| *A61K 38/00* | (2006.01) |

(52) U.S. Cl.
CPC .............. *C12N 9/86* (2013.01); *A61K 31/407* (2013.01); *A61K 31/496* (2013.01); *A61K 31/546* (2013.01); *A61K 38/50* (2013.01); *C12Y 305/02006* (2013.01); *A61K 38/00* (2013.01)

(58) Field of Classification Search
None
See application file for complete search history.

(56) References Cited

U.S. PATENT DOCUMENTS 10,982,205 B2 *  4/2021  De Gunzburg ......... A61P 43/00
10,988,749 B2 *  4/2021  De Gunzburg ...... A61K 31/546

FOREIGN PATENT DOCUMENTS

| WO | WO-2017/144495 A1 | 8/2017 |
|---|---|---|
| WO | WO-2017/144496 A1 | 8/2017 |

OTHER PUBLICATIONS

UniProt Database Accession No. A0A5C8ZXF5, Feb. 2020, 1 page (Year: 2020).*
GenBank Database Accession No. WP_063865196, May 2016, 1 page (Year: 2016).*
Goswami et al., Front. Onc. 9:297, 2019, 25 pages (Year: 2019).*
Borgianni et al "Mutational Analysis of VIM-2 Reveals an Essential Determinant for Metallo-β-Lactamase Stability and Folding" Antimicrobial Agents and Chemotherapy vol. 54, pp. 3197-3204, 2010.
Garau et al "Update of the Standard Numbering Scheme for Class B β-Lactamases" Antimicrobial Agents and Chemotherapy vol. 48, pp. 2347-2349, 2004.
Kaase et al. "Pseudomonas Aeruginosa Strain 15307 Subclass B1 Metallo-Beta-Lactamase VIM-46 (blaVIM) Gene, blaVIM-46 Allele, Complete CDs" GenBank Database Accession No. KP749829, 2016.
Makena et al "Comparison of Verona Integron-Borne Metallo-β-Lactamase (VIM) Variants Reveals Differences in Stability and Inhibition Profiles" Antimicrobial Agents and Chemotherapy vol. 60, pp. 1377-1384, 2016.
Meini et al. "Evolution of Metallo-β-Lactamases: Trends Revealed by Natural Diversity and In Vitro Evolution" Antibiotics vol. 3, pp. 285-316, 2014.
Palzkill "Metallo-β-Lactamase Structure and Function" Annals of the New York Academy of Sciences vol. 1277, pp. 91-104, 2013.

* cited by examiner

*Primary Examiner* — David Steadman
(74) *Attorney, Agent, or Firm* — Cesari & McKenna, LLP

(57) ABSTRACT

The present invention relates to an isolated polypeptide having beta-lactamase activity and nucleic acid sequences encoding the polypeptide. The isolated polypeptide of the invention is a VIM-2 variant with improved properties such as improved protease stability, stability in intestinal medium, improved activity against one or more antibiotics, improved specific activity and/or improved production in a host cell.

16 Claims, 1 Drawing Sheet
Specification includes a Sequence Listing.

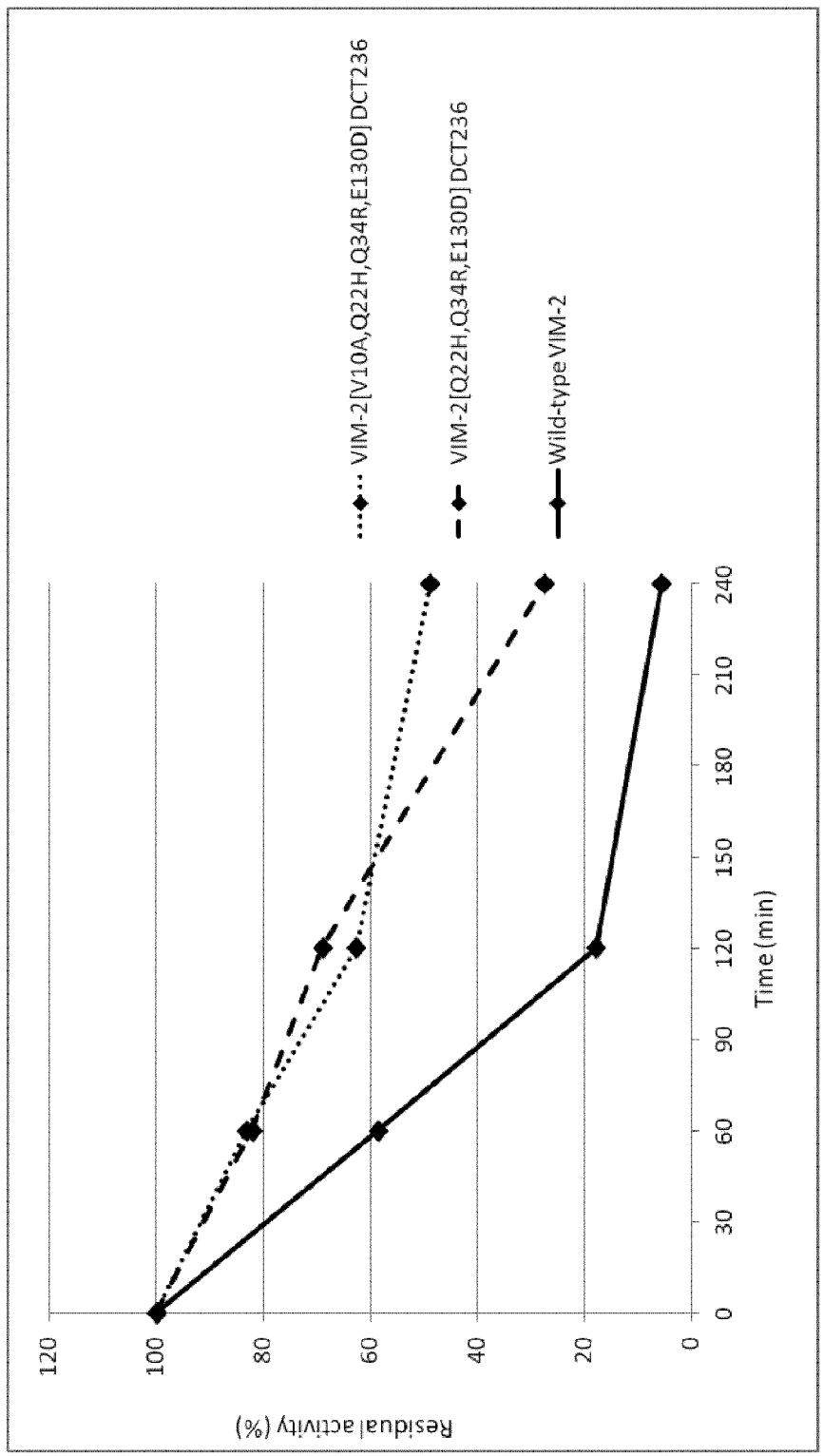

BETA-LACTAMASE VARIANTS

CROSS-REFERENCE TO RELATED APPLICATIONS

This application is the National Stage of International Application No. PCT/EP2018/079223, filed Oct. 24, 2018, which claims the benefit of priority of European Patent Application No. 17198414.9, filed Oct. 25, 2017, the contents of both being incorporated by reference in their entirety for all purposes.

FIELD OF THE INVENTION

The present invention relates to an isolated polypeptide having beta-lactamase activity and nucleic acid sequences encoding the polypeptide. The isolated polypeptide of the invention is a subclass B1 metallo-beta-lactamase belonging to the VIM-type subgroup with improved properties such as improved protease stability, improved intrinsic stability such as thermal stability, improved activity against one or more beta-lactam compounds such as beta-lactam antibiotics, and/or improved production in a host cell.

BACKGROUND OF THE INVENTION

Many antibacterial products, in particular antibiotics, may be used in the treatment of bacterial infections. However, antibiotics do not only attack pathogens at the infection site, but also affect the normal bacterial flora which can be found in healthy subjects, and in particular in the gut. The alteration by antibiotics of the colonic commensal flora (also called colonic microbiota), which is composed of more than ten trillion bacteria from over 500 species, may lead to adverse side effects such as selection of resistant bacteria and potential colonization by resistant bacteria, disruption of normal digestive processes, colonization and infection of the intestine by opportunistic intestinal pathogens such as *Clostridium difficile*, antibiotic-associated diarrhea or other diseases related to the intestinal dysbiosis such as alteration of immunity, metabolic disorders or allergies. These side effects can be reduced by administering enzymes capable of degrading residual active antibiotics in the intestine, more particularly in the late ileum and colon. This approach is described in particular in WO2004/016248 or US20050249716.

However, enzymes are fragile macromolecules whose integrity and catalytic activity are sensitive to a number of physico-chemical factors, such as the presence of proteases leading to their degradation, temperature, ionic strength, availability of metal cofactors or presence of chelators. In addition, enzymes with improved specific activity would be advantageous in order to increase their efficiency and/or reduce the amount necessary to use for obtaining an efficient degradation of residual active antibiotics in a patient in need thereof. Finally, it would be advantageous to obtain improved production yields for such antibiotic-degrading enzymes.

SUMMARY OF THE INVENTION

The present invention provides novel variants of the VIM-2 metallo-beta-lactamase. Specifically, the present invention relates to a polypeptide having beta-lactamase activity, which comprises an amino acid sequence having at least 70% sequence identity to the amino acid sequence shown in SEQ ID NO:1 (which is the sequence of wild-type VIM-2 without its natural signal peptide). The polypeptide of the invention has one or more of the following properties as compared to the wild-type VIM-2 enzyme: (i) improved protease resistance, in particular digestive protease resistance, (ii) improved stability, in particular thermal stability and/or stability in intestinal medium, (iii) improved spectrum of action on beta-lactams (i.e. the variant is able to hydrolyze a greater number of beta-lactam compounds, in particular beta-lactam antibiotics), (iv) improved enzymatic activity on one or more beta-lactam compounds (e.g. on one or more beta-lactam antibiotics), in particular translating in a decreased antibiotic inactivation time, and (v) improved production yield. More specifically, the polypeptide of the invention is a VIM-2 variant that comprises at least one substitution in position 10, with reference to the sequence of the VIM-2 beta-lactamase of SEQ ID NO:1. In another embodiment, the polypeptide of the invention is a VIM-2 variant that comprises substitutions in position 10 and in at least one position selected from positions 22, 34 and 130, wherein the positions correspond to the amino acid positions of the VIM-2 beta-lactamase of SEQ ID NO:1.

In a particular embodiment of the invention, the polypeptide comprises a substitution at positions 10 and 22, at positions 10 and 34, at positions 10 and 130, at positions 10, 22 and 34; at positions 10, 22 and 130; at positions 10, 34 and 130, or at positions 10, 22, 34 and 130.

It is also herein disclosed a VIM-2 variant comprising a substitution in at least one position selected from positions 10, 22, 34 and 130, wherein the positions correspond to the amino acid positions of the VIM-2 beta-lactamase of SEQ ID NO:1.

In a particular embodiment of the invention, the substitution at position 10 is VIM. In another embodiment, the substitution at position 22 is Q22H or Q22N. In another embodiment, the substitution at position 34 is Q34R. In another embodiment, the substitution at position 130 is E130D.

Bacteria producing the VIM-2 variant according to the invention may present an improved property with respect to a Minimal Inhibitory Concentration (MIC) for at least one beta-lactam antibiotic such as, but not exclusively, ampicillin, piperacillin, ticarcillin, temocillin, cephalothin, cefoxitin, cefuroxime, cefotaxime, ceftazidime, cefepime, ceftriaxone, ceftaroline, cefotetan, imipenem, meropenem and ertapenem, as compared to a MIC of the same bacteria producing wild-type VIM-2 of SEQ ID NO:1, which may be determined by using standard in vitro susceptibility testing methods, such as the microdilution broth method (Clinical Laboratory Standard Institute, document M07-A10: Methods for Dilution Antimicrobial Susceptibility Tests for Bacteria That Grow Aerobically; Approved Standard—Tenth Edition). In the context of the present invention, the expression "improved property with respect to a Minimal Inhibitory Concentration (MIC)" denotes a MIC which is increased for the bacteria producing the VIM-2 variant, for example a MIC increased 2-fold or more, compared with the same bacteria producing the wild-type VIM-2.

The VIM-2 variant according to the invention may also present an improved property with respect to resistance to proteases, in particular to digestive proteases, as compared with wild-type VIM-2 of SEQ ID NO:1, which may be determined by monitoring the enzyme activity (by means of in vitro enzyme assays as described below) and/or integrity (e.g. by means of mass spectrometry analysis) after incubation with either purified proteases such as trypsin, chymotrypsin or the like or with intestinal medium from piglets, pigs, other mammals (such as human intestinal medium) or other animals.

The VIM-2 variant according to the invention may also present an improved property with respect to stability (in particular thermal stability), as compared with wild-type VIM-2 of SEQ ID NO:1, which may be determined by monitoring the enzyme residual activity after incubation of the protein sample (including crude extracts) at temperatures ranging from 45 to 75° C. for up to two hours, and in particular at 65° C. for 45 min. Alternatively, the temperature-induced denaturation could be followed using circular dichroism measurements. This experiment yields an experimental melting temperature (Tm) which is higher for enzymes showing an improved conformational stability.

The VIM-2 variant according to the invention may also present an improved property with respect to stability in intestinal medium, particularly jejunal, ileal and caecal medium, as compared with wild-type VIM-2 of SEQ ID NO:1, which may be determined by monitoring the enzyme residual activity after incubation of the protein sample (including the purified enzyme) for different durations in intestinal medium, for example ileal medium.

The VIM-2 variant according to the invention may also present an improved property with respect to its catalytic activity on one or more beta-lactam substrate(s) (such as specific beta-lactam antibiotic(s)), as compared to the activity shown by the wild-type VIM-2 of SEQ ID NO:1, which may be determined by in vitro enzyme assays, in which the time-dependent variation of a beta-lactam substrate concentration (hydrolysis rate) is monitored spectrophotometrically in the presence of protein samples containing the wild-type VIM-2 or the VIM-2 variant.

The VIM-2 variant according to the invention may also present an improved property with respect to its catalytic parameters such as the $k_{cat}$ and $K_m$ values, as compared to the activity shown by the wild-type VIM-2 of SEQ ID NO:1.

The VIM-2 variant according to the invention may also present an improved property with respect to an increased production level thereof in recombinant bacteria or other suitable hosts, as compared to the production level of wild-type VIM-2 of SEQ ID NO:1, which may be determined by in vitro enzyme assays, for example assays carried out as described above with extracts obtained from bacterial cultures producing the wild-type VIM-2 or the variants thereof. In a particular embodiment, the extract is obtained either as a crude extract following cell or bacteria lysis or in a cell (prokaryotic or eukaryotic) culture medium (in case of a secreted enzyme). All these methods may also be implemented on a purified enzyme.

In a particular embodiment, the polypeptide of the invention is selected from the group consisting of SEQ ID NO:3 to SEQ ID NO:23.

```
VIM-2 V10A
                                            (SEQ ID NO: 3)
VDSSGEYPTASEIPVGEVRLYQIADGVWSHIATQSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLEGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTNRSVVE
```

```
VIM-2 V10A Q34R Q22H
                                            (SEQ ID NO: 4)
VDSSGEYPTASEIPVGEVRLYHIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLEGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTNRSVVE

VIM-2 V10A Q34R Q22N
                                            (SEQ ID NO: 5)
VDSSGEYPTASEIPVGEVRLYNIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLEGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTNRSVVE

VIM-2 V10A Q34R E130D
                                            (SEQ ID NO: 6)
VDSSGEYPTASEIPVGEVRLYQIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLDGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTNRSVVE

VIM-2 V10A Q34R E130D Q22N
                                            (SEQ ID NO: 7)
VDSSGEYPTASEIPVGEVRLYNIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLDGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTNRSVVE

VIM-2 V10A Q34R E130D Q22H
                                            (SEQ ID NO: 8)
VDSSGEYPTASEIPVGEVRLYHIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLDGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTNRSVVE

VIM-2 V10A Q34R Q22H DCT236
                                            (SEQ ID NO: 9)
VDSSGEYPTASEIPVGEVRLYHIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLEGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTN

VIM-2 V10A Q34R Q22N DCT236
                                           (SEQ ID NO: 10)
VDSSGEYPTASEIPVGEVRLYNIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLEGLSSSGDAVRFGPV
```

ELFYPGAAHSTDNLVVYVPSASVLYGGCAIYELSRTSAGNVADADLAE

WPTSIERIQQHYPEAQFVIPGHGLPGGLDLLKHTTNVVKAHTN

VIM-2 V10A Q34R E130D DCT236
(SEQ ID NO: 11)
VDSSGEYPTASEIPVGEVRLYQIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLDGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTN

VIM-2 V10A Q34R E130D Q22N DCT236
(SEQ ID NO: 12)
VDSSGEYPTASEIPVGEVRLYNIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLDGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTN

VIM-2 V10A Q34R E130D Q22H DCT236
(SEQ ID NO: 13)
VDSSGEYPTASEIPVGEVRLYHIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLDGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTN

In a particular embodiment, the polypeptide of the invention is a functional variant of the VIM-2 beta-lactamase of any one of SEQ ID NO:3 to 13, further comprising a V1M substitution. Accordingly, the invention also relates to a polypeptide comprising or consisting of the amino acid sequence shown in SEQ ID NO:14-23.

VIM-2 V10A V1M Q34R Q22H
(SEQ ID NO: 14)
MDSSGEYPTASEIPVGEVRLYHIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLEGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTNRSVVE

VIM-2 V10A V1M Q34R Q22N
(SEQ ID NO: 15)
MDSSGEYPTASEIPVGEVRLYNIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLEGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTNRSVVE

VIM-2 V10A V1M Q34R E130D
(SEQ ID NO: 16)
MDSSGEYPTASEIPVGEVRLYQIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLDGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTNRSVVE

VIM-2 V10A V1M Q34R E130D Q22N
(SEQ ID NO: 17)
MDSSGEYPTASEIPVGEVRLYNIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLDGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTNRSVVE

VIM-2 V10A V1M Q34R E130D Q22H
(SEQ ID NO: 18)
MDSSGEYPTASEIPVGEVRLYHIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLDGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTNRSVVE

VIM-2 V10A V1M Q34R Q22H DCT236
(SEQ ID NO: 19)
MDSSGEYPTASEIPVGEVRLYHIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLEGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTN

VIM-2 V10A V1M Q34R Q22N DCT236
(SEQ ID NO: 20)
MDSSGEYPTASEIPVGEVRLYNIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLEGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTN

VIM-2 V10A V1M Q34R E130D DCT236
(SEQ ID NO: 21)
MDSSGEYPTASEIPVGEVRLYQIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLDGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTN

VIM-2 V10A V1M Q34R E130D Q22N DCT236
(SEQ ID NO: 22)
MDSSGEYPTASEIPVGEVRLYNIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLDGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTN

-continued

VIM-2 V10A V1M Q34R E130D Q22H DCT236
(SEQ ID NO: 23)
MDSSGEYPTASEIPVGEVRLYHIADGVWSHIATRSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLDGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTN

The present invention also relates to a nucleic acid sequence encoding the VIM-2 polypeptide variant of the invention, nucleic acid constructs comprising the same, recombinant viruses or host cells (prokaryotic and eukaryotic) comprising the nucleic acid sequence or the nucleic acid construct according to the invention, and methods for their production.

The invention further relates to a composition comprising the polypeptide variant according to the invention. In a particular embodiment, the composition is orally administrable and is able to release the polypeptide in a desired part of the intestine of a subject in need thereof. Preferably, the desired part is the jejunum, ileum, caecum or colon.

In a further embodiment, the invention relates to a recombinant host cell, prokaryotic or eukaryotic, or organism producing the polypeptide that may be administered to a subject and release the polypeptide in the desired part of the intestine of said subject in need thereof. Preferably the polypeptide is released in the ileum, caecum or colon, preferably the caecum or colon.

A further aspect of the invention is a kit-of-parts for separate, sequential or simultaneous administration of the polypeptide according to the invention and a beta-lactam compound, for example beta-lactam antibiotic, which is sensitive to said polypeptide of the kit-of-parts. In a particular embodiment, both the polypeptide and the antibiotic are orally administrable. In another embodiment, the polypeptide and the antibiotic are administered by different routes, for instance the polypeptide is orally administrable and the antibiotic is parenterally administrable, such as by injection like an intravenous, intra-arterial, intramuscular, subcutaneous or intraperitoneal injection. In a particular embodiment, the polypeptide is administered before or after, in particular before, the antibiotic.

The present invention also relates to methods of therapy implementing the polypeptide of the invention. Thus the invention provides the polypeptide of the invention, which is a VIM-2 variant, for use as a medicament. It more specifically provides the use of said polypeptide or a composition or a kit-of-parts containing the same, in a method for inactivating a beta-lactam antibiotic in a subject in need thereof. The invention also relates to the use of the polypeptide, the composition or the kit-of-parts of the invention, in a method for the treatment of a bacterial infection which is caused by bacteria which are susceptible to a beta-lactam antibiotic. More particularly, the bacterial infection is treated by using a combination of the polypeptide of the invention and of a beta-lactam antibiotic which is sensitive to said polypeptide, thereby having the infection treated thanks to the beta-lactam antibiotic whereas any unwanted residual active antibiotic is eliminated from the intestine, and in a specific embodiment specifically from the jejunum, ileum, caecum and colon, thanks to the polypeptide of the invention. In this particular embodiment, the polypeptide is preferably formulated in a composition that is able to release the polypeptide in a desired part of the intestine of a subject in need of such bacterial infection treatment, wherein the desired part of the intestine is preferably the jejunum, the ileum, the caecum or the colon, most preferably the ileum, the caecum or the colon. The polypeptide may be produced by recombinant host cells (prokaryotic or eukaryotic) or organisms that are orally administered to the subject in need of such bacterial infection treatment, and release the polypeptide in the desired part of the intestine, in particular in the ileum, caecum or colon.

DETAILED DESCRIPTION OF THE INVENTION

The present invention provides novel variants of the VIM-2 metallo-beta-lactamase. Therefore, the sequence of the polypeptide of the invention is not identical to the sequence of VIM-2 which is shown in SEQ ID NO:1 in that it differs from VIM-2 by at least one amino acid modification as compared to SEQ ID NO:1.

The sequence shown in SEQ ID NO:1 is the amino acid sequence of wild-type VIM-2 that has undergone N-terminal signal peptide cleavage (i.e. the sequence of wild-type VIM-2 without its signal peptide).

SEQ ID NO: 1:
VDSSGEYPTVSEIPVGEVRLYQIADGVWSHIATQSFDGAVYPSNGLIV

RDGDELLLIDTAWGAKNTAALLAEIEKQIGLPVTRAVSTHFHDDRVGG

VDVLRAAGVATYASPSTRRLAEVEGNEIPTHSLEGLSSSGDAVRFGPV

ELFYPGAAHSTDNLVVYVPSASVLYGGCAIYELSRTSAGNVADADLAE

WPTSIERIQQHYPEAQFVIPGHGLPGGLDLLKHTTNVVKAHTNRSVVE

This sequence thus starts with a valine residue at its N-terminal end. However, in particular embodiments of the invention, this first valine residue may be replaced by a methionine residue. For example, in cases where the VIM-2 protein or its variant are produced without an N-terminal signal peptide from an expression cassette, an initiation codon encoding a methionine residue may be introduced in the VIM-2 or VIM-2 variant coding gene instead of a codon encoding a valine residue. Accordingly, in a particular embodiment of the invention, the polypeptide of the invention comprises the V1M substitution.

The polypeptide of the present invention shares at least 70% sequence identity with the amino acid sequence shown in SEQ ID NO:1, said polypeptide having one or more of the following properties as compared to the wild-type VIM-2 enzyme: (i) improved resistance to proteases (in particular digestive proteases), (ii) improved stability (in particular thermal stability and/or stability in intestinal medium), (iii) improved spectrum of action on beta-lactam compounds in particular beta-lactam antibiotics, (i.e. the polypeptide of the invention is able to inactivate a greater number of different beta-lactam compounds (such as antibiotics) as compared to the wild-type VIM-2 enzyme, or it is able to inactivate beta-lactam compounds not susceptible to the wild-type VIM-2 enzyme), (iv) improved enzymatic activity (in particular decreased antibiotic inactivation time), and (v) improved production yield.

The variant polypeptide of the invention comprises a substitution in at least one position selected from positions 10, 22, 34 and 130, wherein the positions correspond to the amino acid positions shown in SEQ ID NO:1. In a particular embodiment, the variant polypeptide of the invention comprises a substitution in position 10. In another particular embodiment, the variant polypeptide of the invention comprises a substitution in position 10 and in at least one position selected from positions 22, 34 and 130. In a further embodiment, the variant polypeptide of the invention comprises a modification in positions 10, 22, 34 and 130, wherein the positions correspond to the amino acid positions of the VIM-2 beta-lactamase of SEQ ID NO:1.

In a particular embodiment, the variant polypeptide comprises the following substitutions:
V10A; and
Q22H, N; and
Q34R; and
E130D.

In the context of the present invention, a coma after a numbered position indicates alternative modifications at said position. For example, "22H, N" means that the amino acid at position 22 in SEQ ID NO:1 may be replaced by H or N.

In a particular embodiment for improving the intestinal stability and specific activity against a range of beta-lactam antibiotics, the polypeptide of the invention comprises the 10A, 22N and 34R substitutions.

In a particular embodiment for improving the intestinal stability and specific activity against a range of beta-lactam antibiotics, the polypeptide of the invention comprises the 10A, 22H and 34R substitutions.

In a particular embodiment for improving the intestinal stability and specific activity against a range of beta-lactam antibiotics, the polypeptide of the invention comprises the 10A, 34R and 130D substitutions.

In a particular embodiment for improving the intestinal stability and enzymatic activity against a range of beta-lactam antibiotics, the polypeptide of the invention comprises the 10A, 22H, 34R and 130D substitutions.

In a particular embodiment for improving the intestinal stability and specific activity against a range of beta-lactam antibiotics, the polypeptide of the invention comprises the 10A, 22N, 34R and 130D substitutions.

In the present invention, amino acids are represented using either the well-known three letter code or one letter code as summarized in the table below.

| Amino acid | Three letter code | One letter code |
|---|---|---|
| Alanine | ala | A |
| Arginine | arg | R |
| Asparagine | asn | N |
| Aspartic acid | asp | D |
| Cysteine | cys | C |
| Glutamic acid | glu | E |
| Glutamine | gln | Q |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |

According to the present invention, a beta-lactamase is a polypeptide having beta-lactamase activity, i.e. an enzyme which catalyzes the irreversible hydrolysis of the amide bond of the beta-lactam ring found in compounds such as beta-lactam antibiotics (e. g. penicillins, cephalosporins, carbapenems, penam sulfones) to create an hydrolyzed molecule devoid of its antibacterial activity.

In the context of the present invention, the VIM-2 beta-lactamase is the polypeptide having the sequence shown in SEQ ID NO:1. This enzyme has been described in 2000 by Poirel et al. (Characterization of VIM-2, a carbapenem-hydrolyzing metallo-beta-lactamase and its plasmid- and integron-borne gene from a Pseudomonas aeruginosa clinical isolate in France; Antimicrob. Agents Chemother. 2000; 44(4): 891-7) and further characterized by Docquier et al. in 2003 (On functional and structural heterogeneity of VIM-type metallo-beta-lactamases. J. Antimicrob. Chemother. 2003; 51:257-266).

The activity of the VIM-2 variant of the invention may be tested by a number of assays. For example, in vitro enzyme assays are implemented, in which the rate of hydrolysis of a beta-lactam compound hydrolysis is determined spectrophotometrically in the presence of protein samples containing the wild-type VIM-2 or a VIM-2 variant. Specifically, the concentration of a beta-lactam compound and/or its hydrolysis product in solution (using a suitable buffer, such as 50 mM HEPES buffer pH 7.5, supplemented with 50 μM $ZnSO_4$) could be followed in a UV-Visible spectrophotometer or microwell plate reader at a wavelength that corresponds to the maximum absorbance of the substrate and/or product. In the presence of a beta-lactamase, the time-dependent variation of the concentration of the beta-lactam substrate and/or product will thus correspond to the reaction rate. If the initial rate of hydrolysis is measured ($[S]_t \approx [S]_0$), this reaction rate (expressed in μM/min or μM/s) is directly proportional to the enzyme concentration in the assayed sample. Furthermore, the variation of the initial rate upon initial substrate concentration is characterized by the Henri-Michaelis-Menten equation and allows to compute the kinetic parameters ($k_{cat}$ and $K_M$) of the enzyme for the hydrolysis of specific beta-lactam compounds. Thus, the measure of the initial rates of hydrolysis as determined in such enzyme assays allows to characterize the properties of samples containing VIM-2 variants, such as its preferential activity towards a specific substrate or its relative abundance in the sample.

In a particular embodiment, the polypeptide of the present invention may be isolated. In the context of the present invention, the term "isolated" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE. In particular, it is preferred that the polypeptides are in "essentially pure form", i.e., that the polypeptide preparation is essentially free of other biochemical components such as polynucleotides, polysaccharides and polypeptides, with which it is natively associated. This could be accomplished, for example, by preparing the polypeptide by means of well-known recombinant methods and by classical purification methods.

The relatedness between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman and Wunsch, 1970, J. Mol. Biol. 48: 443-453. The substitution matrix used is BLOSUM62, gap opening penalty is 10, and gap extension penalty is 0.5.

The degree of identity between an amino acid sequence of the present invention and the amino acid sequence referred to in the claims (SEQ ID NO:1) is calculated as the number of exact matches in an alignment of the two sequences, divided by the length of the "invention sequence" or the length of SEQ ID NO:1, whichever is the shortest. The result is expressed in percent identity.

An exact match occurs when the "invention sequence" and SEQ ID NO:1 have identical amino acid residues in the same positions of the alignment. The length of a sequence is the number of amino acid residues in the sequence (e.g., the length of amino acids 1-240 of SEQ ID NO:1 is 240).

In particular embodiments of the present invention, the degree of identity of those particular peptides to SEQ ID NO:1 is at least 70%, 75%, 80%, 85%, 90%, 91%, 92%, 93%, 94%, 95%, 96%, 97%, 98% or at least 99%. In still further embodiments, their degree of identity to SEQ ID NO:1 is of at least 88.7%, 89.1%, 89.5%, 89.8%, 90.2%, 90.6%, 91%, 91.4%, 91.7%, 92.1%, 92.5%, 92.9%, 93.2%, 93.6%, 94%, 94.4%, 94.7%, 95.1%, 95.5%, 95.9%, 96.2%, 96.6%, 97%, 97.4%, 97.7%, 98.1%, 98.5%, 98.9%, 99.2% or at least 99.6%.

Of course, the VIM-2 variant of the present invention may further comprise a number of modifications relative to SEQ ID NO:1 in positions different from those specifically identified above. Further modifications may include amino acid substitutions, deletions or insertions, as well as combinations of any number of such modifications. In a particular embodiment, such modifications of the VIM-2 variant of the present invention include amino acid deletions in the amino-terminal or carboxy-terminal end of the protein, in addition to those specifically identified above. In an illustrative, non-limiting embodiment, the polypeptide of the invention may be deleted of 1, 2, 3, 4, 5, 6, or 7 amino acids located at the carboxy-terminal end of the protein, as compared to SEQ ID NO:1. In a preferred embodiment, the polypeptide of the invention presents a carboxy-terminal truncation from position 237 of SEQ ID NO:1. In the context of the invention, this means that amino acid residues 237 to 240 of SEQ ID NO:1 are absent from the resulting polypeptide of the invention. In another embodiment, the polypeptide of the invention presents a carboxy-terminal truncation of residues 236-240 of SEQ ID NO:1. In another embodiment, the polypeptide of the invention presents a C-terminal truncation of residues 235-240 of SEQ ID NO:1. In another illustrative, non-limiting embodiment, the polypeptide of the invention may be deleted of one or more than one (such as 1, 2, 3, 4, 5, 6 or 7 amino acids located at the amino-terminal end of the protein, as compared to SEQ ID NO:1, i.e. as compared to a sequence of wild-type VIM-2 that has undergone N-terminal signal peptide cleavage (i.e. the sequence of wild-type VIM-2 without its signal peptide). In a specific variant of this embodiment, the polypeptide that is deleted (or, otherwise stated, that has a truncation) of one or more than one amino acids located at the amino-terminal end as compared to SEQ ID NO:1 may further comprise an insertion or extension as is defined below, such as a tag or a signal peptide.

In the context of the present invention, the term "insertion" is intended to also cover amino- and/or carboxy-terminal extensions. In a particular embodiment, N-terminal extensions may include the addition of a signal peptide to the polypeptide of the invention. This may include the natural signal peptide of wild-type VIM-2 having the amino acid sequence MFKLLSKLLVYLTASIMAIASPLAFS (SEQ ID NO:2) or a modified signal peptide having either of substitution L9S, L9F, L9W, V10I, L12C, A14V, I16T, M17L, I19M, I19T, F25C when compared to that of wild-type VIM-2, or any combination of the above mentioned substitutions, or any other appropriate signal peptide, or both.

Representative N-terminal or C-terminal extensions may include the addition of non-naturally occurring amino acid(s), such as "tag" peptides encoded by a DNA fragment cloned in fusion with the wild-type VIM-2 or any variant thereof, which allows facilitating the identification and/or purification of the polypeptide of the invention. Such appropriate tag may include histidine tags (6×His) or glutathione-S-transferase or maltose-binding protein, for example, as is well known in the art.

A polypeptide according to the invention may present a specific activity for a given beta-lactam antibiotic improved as compared to the specific activity exhibited by wild-type VIM-2 of SEQ ID NO:1 for the same antibiotic. In a particular embodiment, the specific activity, expressed in nmoles of substrates hydrolyzed per unit of time and per one mg of a protein sample containing the polypeptide of the present invention is at least 105%, relative to the specific activity of the wild-type VIM-2 of SEQ ID NO:1 determined using the same procedure exposed in the example section. In a further embodiment, the relative specific activity of the polypeptide of the present invention is at least 110, 115, 120, 125, 130, 135, 140, 145, 150, 160, 170, 180, 190, 200, 220, 240, 260, 280, 300, 350, 400, 500, 600, 700, 800 or even at least 1600%, still relative to the specific activity of wild-type VIM-2 of SEQ ID NO:1.

In a further particular embodiment, the polypeptide of the invention comprises, or consists of, the amino acid sequence of any one of SEQ ID NO: 3 to 23, or a fragment thereof having beta-lactamase activity (such as a fragment lacking 1, 2, 3, 4, 5, 6 or 7, or more than 7 C-terminal amino acids as compared to the polypeptide of any one of SEQ ID NO:3 to 23), in particular a fragment lacking amino acids 237-240, 236-240 or 235-240 as described above. In a variant of this embodiment, the polypeptide without a signal peptide may comprise a further amino acid substitution. In a variant of this embodiment, the polypeptide further comprises a signal peptide (such as the signal peptide shown in SEQ ID NO:2 or any variant thereof as defined above) at its N-terminal end.

In a particular embodiment, the polypeptide of the invention comprises:
(i) a C-terminal truncation of residues 236-240 of SEQ ID NO:1, and
(ii) a substitution at each of positions 10 and 22;
a substitution at each of positions 10 and 34;
a substitution at each of positions 10 and 130;
a substitution at each of positions 10, 22 and 34;
a substitution at each of positions 10, 22 and 130;
a substitution at each of positions 10, 34 and 130; or
a substitution at each of positions 10, 22, 34 and 130.

In a further particular embodiment, the polypeptide of the invention comprises a C-terminal truncation of residues 236-240 of SEQ ID NO:1 and a substitution at each of positions 10, 22, 34 and 130.

In a particular embodiment, the polypeptide of the invention comprises a C-terminal truncation of residues 236-240 and at least one modification selected from V10A, Q22H or Q22N, Q34R and E130D.

The present invention also relates to a nucleic acid molecule comprising a nucleic acid sequence which encodes a VIM-2 polypeptide variant of the invention.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose gel electrophoresis or any other appropriate method. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The nucleic acid sequences of the invention can be prepared by introducing at least one mutation into a template sequence encoding wild-type VIM-2 of SEQ ID NO:1 or a subsequence thereof, wherein the mutant nucleic acid sequence encodes a variant VIM-2 polypeptide. The introduction of a mutation into the nucleic acid sequence to exchange one nucleotide for another nucleotide may be accomplished by any of the methods known in the art, e.g., by site-directed mutagenesis, by random mutagenesis, or by doped, spiked, or localized random mutagenesis.

Random mutagenesis is suitably performed either as localized or region-specific random mutagenesis in at least three parts of the gene translating to the amino acid sequence shown in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the polypeptide by any technique, using, e.g., PCR, LCR or any DNA polymerase and ligase, or other DNA processing/modifying enzyme, such as a topoisomerase, as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent VIM-2 sequence in question. This may, e.g., be advantageous when certain regions of the enzyme have been identified to be of particular importance for a given property of the enzyme.

Alternative methods for providing variants of the invention include gene shuffling e.g., as described in WO 95/22625 or in WO 96/00343, and the consensus derivation process as described in EP 897985.

The invention further relates to a nucleic acid construct comprising a nucleic acid sequence of the present invention operably linked to one or more control sequences which direct the expression of the coding sequence in a suitable host cell under conditions compatible with the control sequences. The term "expression" will be understood to include any step involved in the production of the polypeptide including, but not limited to, transcription, post-transcriptional modification, translation, post-translational modification, and secretion.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention. In a particular embodiment, the nucleic acid construct or expression cassette is comprised within a plasmid (such as an expression plasmid).

The term "control sequences" is defined herein to include all components which are necessary or advantageous for the expression of a polynucleotide encoding a polypeptide of the present invention. Each control sequence may be native or foreign to the nucleotide sequence encoding the polypeptide. Such control sequences include, but are not limited to, a leader, an operator, propeptide sequence, promoter, transcription initiation sequence, translation initiation sequence, signal peptide sequence, translation termination sequence, polyadenylation sequence and transcription terminator. At a minimum, the control sequences include a promoter, and transcriptional termination signal, and translational initiation and termination signals. The control sequences may be provided with linkers for the purpose of introducing specific restriction sites facilitating ligation of the control sequences with the coding region of the nucleotide sequence encoding a polypeptide.

The term "operably linked" denotes herein a configuration in which a control sequence is placed at an appropriate position relative to the coding sequence of the polynucleotide sequence such that the control sequence directs the expression of the coding sequence of a polypeptide.

When used herein the term "coding sequence" (CDS) means a nucleotide sequence, which directly specifies the amino acid sequence of its protein product. The boundaries of the coding sequence are generally determined by an open reading frame, which usually begins with the ATG start codon or alternative start codons such as GTG and TTG, and usually terminates with a stop codon such as TAA, TGA or TAG. The coding sequence may consist in a DNA, cDNA; it may be natural, semisynthetic or synthetic; it may also contain unnatural or modified nucleotides.

The term "expression" includes any step involved in the production of the polypeptide including, but not limited to, transcription, post-transcriptional modification, translation, post-translational modification, and secretion.

The term "expression vector" is defined herein as a linear or circular DNA molecule that comprises a polynucleotide encoding a polypeptide of the invention, which is operably linked to additional nucleotides that provide for its expression.

A nucleic acid sequence encoding a polypeptide of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding a polypeptide according to the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. It may also remain in the cell as an autonomously replicating extra-chromosomal DNA molecule, such as a plasmid.

The invention further relates to a host cell comprising the nucleic acid sequence or the nucleic acid construct of the invention. A "host cell", as used herein, includes any cell type, prokaryotic or eukaryotic, which is susceptible to transformation, transfection, transduction, infection and the like with a nucleic acid construct comprising a polynucleotide of the present invention.

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector. The term "host cell" encompasses any progeny of a parent cell that is not identical to the parent cell due to mutations that occur during replication. The choice of a host cell will to a large extent depend upon the gene encoding the polypeptide and its source.

The host cell may consist in or originate from a unicellular or polycellular organism, and may be prokaryotic or eukaryotic.

Among useful unicellular microorganisms are bacterial cells such as Gram-positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* and *Streptomyces murinus*, or Gram-negative bacteria such as *Escherichia coli* and *Pseudomonas* spp.

The introduction of a vector into a bacterial host cell may, for instance, be effected by protoplast transformation (see, e.g., Chang and Cohen, 1979, Molecular General Genetics 168: 111-115), by DNA transformation using competent cells (see, e.g., Young and Spizizin, 1961, Journal of Bacteriology 81: 823-829, or Dubnau and Davidoff-Abelson, 1971, Journal of Molecular Biology 56: 209-221) using any method of transformation including but not limited to chemical transformation or electroporation (see, e.g., Shigekawa and Dower, 1988, Biotechniques 6: 742-751), or conjugation (see, e.g., Koehler and Thorne, 1987, Journal of Bacteriology 169: 5771-5278).

The host cell may also be from a eukaryote, such as an animal, and in particular mammalian, an insect, a plant, or cell-lines derived thereof, or a unicellular eukaryote or fungal cell. The recombinant protein may also be produced in a multicellular organism, such as an animal, in particular a mammal, or a plant.

In a particular embodiment, the host cell may be a fungal cell. In a particular embodiment, the fungal host cell is *Saccharomyces cerevisiae* or *Pichia pastoris*. In a particular embodiment, the host cell is a cell line originating from Chinese Hamster Ovary cells.

Fungal cells may be transformed by a process involving protoplast formation, transformation of the protoplasts, and regeneration of the cell wall in a manner known per se. Yeast may be transformed using the procedures described by Becker and Guarente, In Abelson, J. N. and Simon, M. I., editors, Guide to Yeast Genetics and Molecular Biology, Methods in Enzymology 194: 182-187, Academic Press, Inc., New York; Ito et al., 1983, Journal of Bacteriology 153: 163; and Hinnen et al., 1978, Proceedings of the National Academy of Sciences USA 75: 1920. Fungal cells may also be transformed by electroporation, or any other suitable method for introducing DNA molecules into a cell.

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). In some cases, the conditions for growth of the host cells, and production of the polypeptide are distinct; in a first phase the host cells are allowed to multiply under appropriate conditions, and in a second phase conditions may be changed to allow optimal production of the polypeptide. If the polypeptide is secreted into the nutrient medium, the polypeptide can be recovered directly from the medium. If the polypeptide is not secreted, it can be recovered from cell lysates.

The resulting polypeptide may be recovered using methods known in the art. For example, the polypeptide may be recovered from the nutrient medium by conventional procedures including, but not limited to, centrifugation, filtration, extraction, adsorption, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing, preparative gel electrophoresis), differential solubility (e.g., ammonium sulfate precipitation) or extraction (see, e.g., Protein Purification, J.-C. Janson and Lars Ryden, editors, VCH Publishers, New York, 1989), or a combination thereof.

The present invention further relates to a composition comprising a polypeptide of the present invention. Appropriate compositions include a polypeptide as defined above, in combination with an acceptable carrier. The compositions may be prepared according to methods well known in the art, and be in the form of liquid or dry compositions. The composition may further include components which stabilize the polypeptide according to the invention such as glycerol.

In a particular embodiment, the composition is a pharmaceutical composition comprising a pharmaceutically acceptable carrier. The composition may be in the form of a composition which is orally administrable and is able to release the polypeptide in a desired part of the gastrointestinal tract of a subject in need thereof. Preferably, the desired part is the stomach, duodenum, jejunum, ileum, caecum or colon. In a preferred embodiment, the desired part of the intestine is the jejunum, the ileum, the caecum or the colon, more preferably the ileum, the caecum or the colon. In the latter case, the composition may include one or more gastro resistant compounds which protect the polypeptide of the invention from gastric juice. Such compositions may include the drug delivery systems described in WO93/13795, WO2004/016248 or US20050249716, among others.

The present invention further relates to a host cell or organism as described above, producing the polypeptide of the present invention, that can be introduced into the desired part of the intestine and is able to release said polypeptide into the desired part of the intestine of a subject in need thereof. In a preferred embodiment, the desired part of the intestine is the ileum, caecum or colon, more preferably the caecum or colon. Therefore, the present invention also relates to a host cell or organism as defined above, for use in a method of therapy as disclosed herein, wherein said host cell is administered to a subject in need thereof.

As mentioned above, the VIM-2 polypeptide variant of the present invention is useful in a number of therapeutic and non-therapeutic uses.

The present invention discloses methods of therapy implementing the polypeptide of the invention, wherein said polypeptide or a composition or a kit-of-parts containing the same in combination with an antibiotic, or a host cell or organism expressing said polypeptide is used in a method for inactivating a beta-lactam compound such as a beta-lactam antibiotic in a subject in need thereof. The method is implemented to treat or prevent the adverse effects of antibiotics such as intestinal dysbiosis, the selection of resistant bacteria, disruption of normal digestive processes, colonization by opportunistic intestinal pathogens such as *Clostridium difficile*, antibiotic-associated diarrhea or other diseases related to the intestinal dysbiosis such as alteration of immunity, metabolic disorders or allergies.

The invention also relates to the use of the polypeptide, the composition, the host cell or organism, or the kit-of-parts of the invention, in a method for the treatment of a bacterial infection which is caused by bacteria which are susceptible to a beta-lactam antibiotic. More particularly, the bacterial infection is treated by using a combination of the polypeptide of the invention and a beta-lactam antibiotic which is sensitive to said polypeptide, thereby having the infection treated thanks to the beta-lactam antibiotic whereas any unwanted residual amount of active antibiotic is eliminated thanks to the polypeptide of the invention. In this particular embodiment, the polypeptide is preferably formulated in a composition that is able to release the polypeptide in a desired part of the intestine of a subject in need of such bacterial infection treatment, wherein the desired part of the intestine is preferably the jejunum, the ileum, the caecum or the colon, most preferably the ileum, the caecum or the colon. The polypeptide may also be released in the desired part of the intestine by a host cell or organism producing said polypeptide, wherein the desired part of the intestine is the ileum, caecum or colon, preferably the caecum or colon. In a particular aspect, the polypeptide, the composition, the host cell or organism, or the kit-of-parts of the invention is used for the treatment of a bacterial infection in a subject that may be an animal, a mammal or a human being whereby an antibiotic sensitive to said polypeptide is administered to the subject before, after or concomitantly with the administration of said polypeptide or composition thereof.

Other uses of the polypeptide of the invention include non-therapeutic uses such as the use of the polypeptide for the remediation of antibiotic in the environment or an environmental setting. Such uses and methods may be found described for example in WO 2012/007536 describing the use of laccases, cellulases and lipases for the remediation of antibiotics in the environment, and are herein applied mutatis mutandis for the elimination of beta-lactam antibiotics from the environment using the polypeptide of the invention.

LEGEND OF THE FIGURES

FIG. 1 is a graph representing the specific activity of wild-type VIM-2, VIM-$2_{[Q22H,Q34R,E130D]DCT236}$ and VIM-$2_{[V10A,Q22H,Q34R,E130D]DCT236}$ variants after 0, 60, 120 and 240 minutes in human ileal extract.

EXAMPLES

Example 1: Production and Purification of VIM-2 Variants

The VIM-2 variant was produced in *Escherichia coli* using either a T7 promoter-based expression system (using the pET-9 expression plasmid). Briefly, the mutant bla$_{VIM-2}$ gene was cloned in the plasmid vector pET-9 using the NdeI and BamHI restriction sites, and the resulting plasmid introduced in *E. coli* BL21(DE3) cells. The resulting host cell was grown in the rich auto-inducing cell culture medium ZYP-5052 (Studier, F. W. 2005. Protein production by auto-induction in high density shaking cultures. Protein Expr. Purif. 41:207-234.) supplemented with ZnSO$_4$ for 24 h. The bacterial cells and the culture supernatant were separated by centrifugation. The clarified culture supernatant was then concentrated using physical (e. g. ultrafiltration) or chemical (precipitation) methods. Alternatively, the protein could be extracted from the bacterial cells, which were resuspended in 100 to 200 ml of 20 mM Tris (pH 8.0) prior to treatment with physical (ultrasonication, French press) or chemical (lysozyme, detergents) agents to induce cell lysis. The cellular extract was clarified by centrifugation. The resulting clarified sample was then loaded on an anion exchange chromatography column. Proteins were eluted using a linear gradient of NaCl in 20 mM Tris buffer (pH 8.0) and the active fractions pooled and concentrated. The protein sample was then loaded on a second anion exchange column and eluted using a linear gradient of NaCl in 20 mM triethanolamine (pH 7.2). The resulting sample was loaded on a gel filtration column and the proteins eluted with 50 mM HEPES (pH 7.5) supplemented with 50 µM ZnSO$_4$ and 150 mM NaCl. The purified protein was then concentrated and stored.

In particular, this production protocol was successfully used to produce the following variant VIM-2 enzyme: VIM-$2_{[,Q22H,Q34R,E130D]}$, VIM-$2_{[,Q22H,Q34R,E130D]DCT236}$ and VIM-$2_{[V10A,Q22H,Q34R,E130D]\ DCT236}$. Another variant that may be produced thanks to a similar method is VIM-$2_{[V10A,Q22H,Q34R,E130D]}$.

Example 2: Determination of Increased Stability of a Variant of VIM-2 in Intestinal Medium To measure the stability of VIM-2 variants, the following procedure is applied: the imipenem-hydrolyzing activity of purified protein samples was determined after incubation in human ileal extract. The specific activity (Sp. Act.) for the variants was measured at different time points (0, 60, 120 and 240 min) during the incubation. The specific activity at time t was compared with the specific activity at time t=0 to assess the loss of activity of the variant in the intestinal extract. The change over time was expressed as the ratio between the initial activity (at t=0) and the activity measured later in time ((Sp. Act. Variant)t/(Sp. Act. Variant)t=0. A value lower than one indicates a loss of activity when incubated in the intestinal extract. The residual activity at different time points are compared to evaluate the greater stability in intestinal extract of some variants compared to the wild-type enzyme.

The specific activity of wild-type VIM-2 enzyme, VIM-2 variant VIM-2$_{[Q22H,Q34R,E130D]DCT236}$ and VIM-2 variant VIM-2$_{[V10A,Q22H,Q34R,E130D]DCT236}$ over time when incubated in ileal extract are presented in FIG. 1.

The loss of activity over time is also summarized in the following table:

| Residual activity after x minutes in ileal extract | 0 | 60 | 120 | 240 |
|---|---|---|---|---|
| Wild-type VIM-2 | 100.0% | 58.5% | 17.8% | 5.6% |
| VIM-2$_{[Q22H, Q34R, E130D] DCT236}$ | 100.0% | 82.1% | 69.0% | 27.5% |
| VIM-2$_{[V10A, Q22H, Q34R, E130D] DCT236}$ | 100.0% | 83.1% | 62.6% | 48.8% |

As shown in the table or FIG. 1, the wild-type enzyme lost 94.4% of its activity after 240 minutes incubation in ileal extract. The VIM-2$_{[Q22H,Q34R,E130D]DCT236}$ and VIM-2$_{[V10A,Q22H,Q34R,E130D]DCT236}$ variants lost only 72.5% and 51.2% of their activity in the same conditions, respectively.

The combination of substitutions Q22H, Q34R, E130D results in variants with dramatically improved properties in an industrial perspective. The addition of substitution V10A improves even further the stability of the enzyme in human ileal extract.

Example 3: Determination of the Specific Enzymatic and or Catalytic Activity of Given VIM-2 Variants Towards Various Beta-Lactams For the variant enzymes produced as mentioned in example 1, it is possible to measure the specific activity and catalytic properties towards specific beta-lactam compounds such as beta-lactam antibiotics.

The variant VIM-2$_{[V10A,Q22H,Q34R,E130D]DCT236}$ exhibits improved catalytic properties in buffer when considering imipenem as a substrate:

| Enzyme | $k_{cat}$ (s$^{-1}$) | $K_M$ (μM) | $k_{cat}/K_M$ (μM$^{-1}$s$^{-1}$) |
|---|---|---|---|
| VIM-2$_{[Q22H, Q34R, E130D] DCT236}$ | 77 | 9 | 8.5 |
| VIM-2$_{[V10A, Q22H, Q34R, E130D] DCT236}$ | 130 | 14 | 9.4 |

The above results illustrate that the VIM-2$_{[V10A,Q22H,Q34R,E130D]DCT236}$ exhibited a strongly improved activity against a carbapenem antibiotic which was unexpected and is of strong industrial interest.

Example 4: Determination of the Enzymatic Activity of Given VIM-2 Variants Towards Various Beta-Lactams after 4 Hours of Incubation in Intestinal Medium The enzymatic activity assessment is performed as described hereafter: after 4 hours incubation of VIM-2 variants in human ileal extract, the hydrolysis of beta-lactams was monitored spectrophotometrically at a suitable wavelength. The enzymatic activity may be expressed in nmol of beta-lactam substrate hydrolyzed by min and per mg of total protein in the sample.

In the following, all the enzymatic activities will be expressed relatively to the enzymatic activity of the wild-type enzyme measured in the same conditions.

For VIM-2$_{[Q22H,Q34R,E130D]DCT236}$ and VIM-2$_{[V10A,Q22H,Q34R,E130D]DCT236}$ variants, the measured enzymatic activities are:

| Enzyme | (Residual Enzymatic activity of the enzyme/Residual Enzymatic activity of the wild-type enzyme) for Piperacillin |
|---|---|
| VIM-2$_{[WT]}$ | 1 |
| VIM-2$_{[Q22H, Q34R, E130D] DCT236}$ | 51.44 |
| VIM-2$_{[V10A, Q22H, Q34R, E130D] DCT236}$ | 198.16 |

| Enzyme | (Residual Enzymatic activity of the enzyme/Residual Enzymatic activity of the wild-type enzyme) for Imipenem |
|---|---|
| VIM-2$_{[WT]}$ | 1 |
| VIM-2$_{[Q22H, Q34R, E130D] DCT236}$ | 20.94 |
| VIM-2$_{[V10A, Q22H, Q34R, E130D] DCT236}$ | 51.55 |

| Enzyme | (Residual Enzymatic activity of the enzyme/Residual Enzymatic activity of the wild-type enzyme) for Meropenem |
|---|---|
| VIM-2$_{[WT]}$ | 1 |
| VIM-2$_{[Q22H, Q34R, E130D] DCT236}$ | 10.52 |
| VIM-2$_{[V10A, Q22H, Q34R, E130D] DCT236}$ | 26.55 |

| Enzyme | (Residual Enzymatic activity of the enzyme/Residual Enzymatic activity of the wild-type enzyme) for Ceftriaxone |
|---|---|
| VIM-2$_{[WT]}$ | 1 |
| VIM-2$_{[Q22H, Q34R, E130D] DCT236}$ | 11.66 |
| VIM-2$_{[V10A, Q22H, Q34R, E130D] DCT236}$ | 18.59 |

The above results illustrate that the VIM-2$_{[V10A,Q22H,Q34R,E130D]DCT236}$ exhibited a strongly improved activity after 4 hours of incubation in human intestinal medium against several beta-lactams of interest compared with the VIM-2$_{[Q22H,Q34R,E130D]DCT236}$ mutant which activity against the same beta-lactams was highly improved compared with the wild-type enzyme.

The combination of substitutions V10A, Q22H, Q34R, E130D therefore results in a variant with dramatically improved properties in an industrial perspective.

The invention claimed is:

1. A polypeptide having beta-lactamase activity, which comprises an amino acid sequence having at least 90% sequence identity to SEQ ID NO:1, said polypeptide comprising:
    a substitution at each of positions 10 and 22;
    a substitution at each of positions 10 and 34;
    a substitution at each of positions 10 and 130;
    a substitution at each of positions 10, 22, and 34;
    a substitution at each of positions 10, 22, and 130;
    a substitution at each of positions 10, 34, and 130; or
    a substitution at each of positions 10, 22, 34, and 130,
    wherein the positions correspond to the positions in the sequence of SEQ ID NO:1, the substitution at position 10 is V10A, the substitution at position 22 is Q22H or Q22N, the substitution at position 34 is Q34R, the substitution at position 130 is E130D, and said polypeptide has improved stability and beta-lactamase activity as compared with wild-type VIM-2 of SEQ ID NO:1.

2. The polypeptide according to claim 1, wherein the residue corresponding to the first residue of SEQ ID NO:1 is replaced with a methionine residue.

3. The polypeptide according to claim 1, further comprising a signal peptide at its N-terminal end.

4. The polypeptide according to claim 1, comprising a truncation at its N-terminal or C-terminal end as compared to the sequence shown in SEQ ID NO:1.

5. The polypeptide according to claim 4, which comprises:
    a C-terminal truncation of residues 237-240 of SEQ ID NO:1;
    a C-terminal truncation of residues 236-240 of SEQ ID NO:1; or
    a C-terminal truncation of residues 235-240 of SEQ ID NO:1.

6. The polypeptide according to claim 1, comprising or consisting of the amino acid sequence of any one of SEQ ID NO:4 to 23 or a fragment thereof having beta-lactamase activity.

7. An isolated nucleic acid comprising a nucleic acid sequence encoding the polypeptide according to claim 1.

8. A nucleic acid construct comprising the nucleic acid of claim 7, operably linked to one or more control sequences that direct the expression of the polypeptide in a suitable expression host.

9. An isolated recombinant host cell, comprising the nucleic acid construct of claim 8.

10. A composition comprising the polypeptide of claim 1.

11. The composition of claim 10, which is orally administrable and is able to release the polypeptide in a desired part of the intestine.

12. A kit-of-parts comprising
    (a) the polypeptide of claim 1; and
    (b) a beta-lactam antibiotic which is sensitive to said polypeptide of (a)
    for separate, sequential, or simultaneous administration.

13. A method for inactivating a beta-lactam antibiotic in a subject in need thereof, comprising administering to said subject a therapeutically effective amount of
the polypeptide of claim 1,
the composition of claim 10,
the kit-of-parts of claim 12, or
the isolated recombinant host cell of claim 9.

14. A method for treating a bacterial infection in a subject in need thereof, comprising administering to said subject a therapeutically effective amount of
the polypeptide of claim 1,
the composition of claim 10,
the kit-of-parts of claim 12, or
the isolated recombinant host cell of claim 9,
wherein when said polypeptide, said composition, or said isolated recombinant host cell is administered, a beta-lactam antibiotic which is sensitive to said polypeptide is administered in combination with said polypeptide, said composition, or said isolated recombinant host cell.

15. The polypeptide according to claim 2, further comprising a signal peptide at its N-terminal end.

16. The composition of claim 11, wherein the desired part of the intestine is the jejunum, the ileum, the caecum, or the colon.

* * * * *

UNITED STATES PATENT AND TRADEMARK OFFICE
CERTIFICATE OF CORRECTION

PATENT NO. : 11,365,403 B2  
APPLICATION NO. : 16/757968  
DATED : June 21, 2022  
INVENTOR(S) : Jean De Gunzburg et al.

Page 1 of 1

It is certified that error appears in the above-identified patent and that said Letters Patent is hereby corrected as shown below:

On the Title Page

First Column, item (71), the address of one of the Applicants has been incorrectly listed. It should read as follows:
--(71) Da Volterra, Paris (FR); Bioaster, Lyon (FR)--

First Column, item (73), the address of one of the Assignees has been incorrectly listed. It should read as follows:
--(73) Da Volterra, Paris (FR); Bioaster, Lyon (FR)--

Signed and Sealed this
Ninth Day of August, 2022

Katherine Kelly Vidal
*Director of the United States Patent and Trademark Office*

SEQUENCE LISTING

<160> NUMBER OF SEQ ID NOS: 23

<210> SEQ ID NO 1
<211> LENGTH: 240
<212> TYPE: PRT
<213> ORGANISM: artificial
<220> FEATURE:
<223> OTHER INFORMATION: wild-type VIM-2

<400> SEQUENCE: 1

Val Asp Ser Ser Gly Glu Tyr Pro Thr Val Ser Glu Ile Pro Val Gly
1               5                   10                  15

Glu Val Arg Leu Tyr Gln Ile Ala Asp Gly Val Trp Ser His Ile Ala
            20                  25                  30

Thr Gln Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Glu Gly Leu Ser Ser Ser Gly Asp Ala Val Arg Phe Gly Pro Val
    130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn Arg Ser Val Val Glu
225                 230                 235                 240

<210> SEQ ID NO 2
<211> LENGTH: 26
<212> TYPE: PRT
<213> ORGANISM: artificial
<220> FEATURE:
<223> OTHER INFORMATION: VIM-2 signal peptide

<400> SEQUENCE: 2

Met Phe Lys Leu Leu Ser Lys Leu Leu Val Tyr Leu Thr Ala Ser Ile
1               5                   10                  15

Met Ala Ile Ala Ser Pro Leu Ala Phe Ser
            20                  25

<210> SEQ ID NO 3
<211> LENGTH: 240
<212> TYPE: PRT
<213> ORGANISM: artificial
<220> FEATURE:

<223> OTHER INFORMATION: VIM-2 variant

<400> SEQUENCE: 3

```
Val Asp Ser Ser Gly Glu Tyr Pro Thr Ala Ser Glu Ile Pro Val Gly
1               5                   10                  15

Glu Val Arg Leu Tyr Gln Ile Ala Asp Gly Val Trp Ser His Ile Ala
            20                  25                  30

Thr Gln Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Glu Gly Leu Ser Ser Ser Gly Asp Ala Val Arg Phe Gly Pro Val
    130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn Arg Ser Val Val Glu
225                 230                 235                 240
```

<210> SEQ ID NO 4
<211> LENGTH: 240
<212> TYPE: PRT
<213> ORGANISM: artificial
<220> FEATURE:
<223> OTHER INFORMATION: VIM-2 variant

<400> SEQUENCE: 4

```
Val Asp Ser Ser Gly Glu Tyr Pro Thr Ala Ser Glu Ile Pro Val Gly
1               5                   10                  15

Glu Val Arg Leu Tyr His Ile Ala Asp Gly Val Trp Ser His Ile Ala
            20                  25                  30

Thr Arg Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110
```

```
Thr Arg Arg Leu Ala Glu Val Glu Gly Asn Glu Ile Pro Thr His Ser
        115                 120                 125

Leu Glu Gly Leu Ser Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn Arg Ser Val Val Glu
225                 230                 235                 240

<210> SEQ ID NO 5
<211> LENGTH: 240
<212> TYPE: PRT
<213> ORGANISM: artificial
<220> FEATURE:
<223> OTHER INFORMATION: VIM-2 variant

<400> SEQUENCE: 5

Val Asp Ser Ser Gly Glu Tyr Pro Thr Ala Ser Glu Ile Pro Val Gly
1               5                   10                  15

Glu Val Arg Leu Tyr Asn Ile Ala Asp Gly Val Trp Ser His Ile Ala
                20                  25                  30

Thr Arg Ser Phe Asp Gly Ala Val Tyr Pro Ser Asn Gly Leu Ile Val
            35                  40                  45

Arg Asp Gly Asp Glu Leu Leu Leu Ile Asp Thr Ala Trp Gly Ala Lys
50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Glu Gly Leu Ser Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn Arg Ser Val Val Glu
225                 230                 235                 240
```

<210> SEQ ID NO 6
<211> LENGTH: 240
<212> TYPE: PRT
<213> ORGANISM: artificial
<220> FEATURE:
<223> OTHER INFORMATION: VIM-2 variant

<400> SEQUENCE: 6

Val Asp Ser Ser Gly Glu Tyr Pro Thr Ala Ser Glu Ile Pro Val Gly
1               5                   10                  15

Glu Val Arg Leu Tyr Gln Ile Ala Asp Gly Val Trp Ser His Ile Ala
            20                  25                  30

Thr Arg Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Asp Gly Leu Ser Ser Ser Gly Asp Ala Val Arg Phe Gly Pro Val
    130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn Arg Ser Val Val Glu
225                 230                 235                 240

<210> SEQ ID NO 7
<211> LENGTH: 240
<212> TYPE: PRT
<213> ORGANISM: artificial
<220> FEATURE:
<223> OTHER INFORMATION: VIM-2 variant

<400> SEQUENCE: 7

Val Asp Ser Ser Gly Glu Tyr Pro Thr Ala Ser Glu Ile Pro Val Gly
1               5                   10                  15

Glu Val Arg Leu Tyr Asn Ile Ala Asp Gly Val Trp Ser His Ile Ala
            20                  25                  30

Thr Arg Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro

```
            65                  70                  75                  80
Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Asp Gly Leu Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
210                 215                 220

His Thr Thr Asn Val Val Lys Ala His Thr Asn Arg Ser Val Val Glu
225                 230                 235                 240

<210> SEQ ID NO 8
<211> LENGTH: 240
<212> TYPE: PRT
<213> ORGANISM: artificial
<220> FEATURE:
<223> OTHER INFORMATION: VIM-2 variant

<400> SEQUENCE: 8

Val Asp Ser Ser Gly Glu Tyr Pro Thr Ala Ser Glu Ile Pro Val Gly
1               5                   10                  15

Glu Val Arg Leu Tyr His Ile Ala Asp Gly Val Trp Ser His Ile Ala
            20                  25                  30

Thr Arg Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Asp Gly Leu Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
```

```
                195                 200                 205
Phe Val Ile Pro Gly His Gly Leu Pro Gly Gly Leu Asp Leu Leu Lys
    210                 215                 220
His Thr Thr Asn Val Val Lys Ala His Thr Asn Arg Ser Val Val Glu
225                 230                 235                 240

<210> SEQ ID NO 9
<211> LENGTH: 235
<212> TYPE: PRT
<213> ORGANISM: artificial
<220> FEATURE:
<223> OTHER INFORMATION: VIM-2 variant

<400> SEQUENCE: 9

Val Asp Ser Ser Gly Glu Tyr Pro Thr Ala Ser Glu Ile Pro Val Gly
1               5                   10                  15

Glu Val Arg Leu Tyr His Ile Ala Asp Gly Val Trp Ser His Ile Ala
                20                  25                  30

Thr Arg Ser Phe Asp Gly Ala Val Tyr Pro Ser Asn Gly Leu Ile Val
            35                  40                  45

Arg Asp Gly Asp Glu Leu Leu Leu Ile Asp Thr Ala Trp Gly Ala Lys
        50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Glu Gly Leu Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn
225                 230                 235

<210> SEQ ID NO 10
<211> LENGTH: 235
<212> TYPE: PRT
<213> ORGANISM: artificial
<220> FEATURE:
<223> OTHER INFORMATION: VIM-2 variant

<400> SEQUENCE: 10

Val Asp Ser Ser Gly Glu Tyr Pro Thr Ala Ser Glu Ile Pro Val Gly
1               5                   10                  15

Glu Val Arg Leu Tyr Asn Ile Ala Asp Gly Val Trp Ser His Ile Ala
                20                  25                  30
```

Thr Arg Ser Phe Asp Gly Ala Val Tyr Pro Ser Asn Gly Leu Ile Val
            35                  40                  45

Arg Asp Gly Asp Glu Leu Leu Leu Ile Asp Thr Ala Trp Gly Ala Lys
 50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
                100                 105                 110

Thr Arg Arg Leu Ala Glu Val Glu Gly Asn Glu Ile Pro Thr His Ser
            115                 120                 125

Leu Glu Gly Leu Ser Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
            195                 200                 205

Phe Val Ile Pro Gly His Gly Leu Pro Gly Gly Leu Asp Leu Leu Lys
            210                 215                 220

His Thr Thr Asn Val Val Lys Ala His Thr Asn
225                 230                 235

<210> SEQ ID NO 11
<211> LENGTH: 235
<212> TYPE: PRT
<213> ORGANISM: artificial
<220> FEATURE:
<223> OTHER INFORMATION: VIM-2 variant

<400> SEQUENCE: 11

Val Asp Ser Ser Gly Glu Tyr Pro Thr Ala Ser Glu Ile Pro Val Gly
 1               5                  10                  15

Glu Val Arg Leu Tyr Gln Ile Ala Asp Gly Val Trp Ser His Ile Ala
                20                  25                  30

Thr Arg Ser Phe Asp Gly Ala Val Tyr Pro Ser Asn Gly Leu Ile Val
            35                  40                  45

Arg Asp Gly Asp Glu Leu Leu Leu Ile Asp Thr Ala Trp Gly Ala Lys
 50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
                100                 105                 110

Thr Arg Arg Leu Ala Glu Val Glu Gly Asn Glu Ile Pro Thr His Ser
            115                 120                 125

Leu Asp Gly Leu Ser Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

```
Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn
225                 230                 235

<210> SEQ ID NO 12
<211> LENGTH: 235
<212> TYPE: PRT
<213> ORGANISM: artificial
<220> FEATURE:
<223> OTHER INFORMATION: VIM-2 variant

<400> SEQUENCE: 12

Val Asp Ser Ser Gly Glu Tyr Pro Thr Ala Ser Glu Ile Pro Val Gly
1               5                   10                  15

Glu Val Arg Leu Tyr Asn Ile Ala Asp Gly Val Trp Ser His Ile Ala
            20                  25                  30

Thr Arg Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Asp Gly Leu Ser Ser Ser Gly Asp Ala Val Arg Phe Gly Pro Val
    130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn
225                 230                 235

<210> SEQ ID NO 13
<211> LENGTH: 235
<212> TYPE: PRT
<213> ORGANISM: artificial
<220> FEATURE:
<223> OTHER INFORMATION: VIM-2 variant

<400> SEQUENCE: 13
```

Val Asp Ser Ser Gly Glu Tyr Pro Thr Ala Ser Glu Ile Pro Val Gly
1               5                   10                  15

Glu Val Arg Leu Tyr His Ile Ala Asp Gly Val Trp Ser His Ile Ala
                20                  25                  30

Thr Arg Ser Phe Asp Gly Ala Val Tyr Pro Ser Asn Gly Leu Ile Val
            35                  40                  45

Arg Asp Gly Asp Glu Leu Leu Leu Ile Asp Thr Ala Trp Gly Ala Lys
        50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
                100                 105                 110

Thr Arg Arg Leu Ala Glu Val Glu Gly Asn Glu Ile Pro Thr His Ser
            115                 120                 125

Leu Asp Gly Leu Ser Ser Gly Asp Ala Val Arg Phe Gly Pro Val
    130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn
225                 230                 235

<210> SEQ ID NO 14
<211> LENGTH: 240
<212> TYPE: PRT
<213> ORGANISM: artificial
<220> FEATURE:
<223> OTHER INFORMATION: VIM-2 variant

<400> SEQUENCE: 14

Met Asp Ser Ser Gly Glu Tyr Pro Thr Ala Ser Glu Ile Pro Val Gly
1               5                   10                  15

Glu Val Arg Leu Tyr His Ile Ala Asp Gly Val Trp Ser His Ile Ala
                20                  25                  30

Thr Arg Ser Phe Asp Gly Ala Val Tyr Pro Ser Asn Gly Leu Ile Val
            35                  40                  45

Arg Asp Gly Asp Glu Leu Leu Leu Ile Asp Thr Ala Trp Gly Ala Lys
        50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
                100                 105                 110

Thr Arg Arg Leu Ala Glu Val Glu Gly Asn Glu Ile Pro Thr His Ser
            115                 120                 125

```
Leu Glu Gly Leu Ser Ser Ser Gly Asp Ala Val Arg Phe Gly Pro Val
            130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
        210                 215                 220

His Thr Thr Asn Val Val Lys Ala His Thr Asn Arg Ser Val Val Glu
225                 230                 235                 240

<210> SEQ ID NO 15
<211> LENGTH: 240
<212> TYPE: PRT
<213> ORGANISM: artificial
<220> FEATURE:
<223> OTHER INFORMATION: VIM-2 variant

<400> SEQUENCE: 15

Met Asp Ser Ser Gly Glu Tyr Pro Thr Ala Ser Glu Ile Pro Val Gly
1               5                   10                  15

Glu Val Arg Leu Tyr Asn Ile Ala Asp Gly Val Trp Ser His Ile Ala
            20                  25                  30

Thr Arg Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Glu Gly Leu Ser Ser Ser Gly Asp Ala Val Arg Phe Gly Pro Val
    130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
        210                 215                 220

His Thr Thr Asn Val Val Lys Ala His Thr Asn Arg Ser Val Val Glu
225                 230                 235                 240

<210> SEQ ID NO 16
```

-continued

<211> LENGTH: 240
<212> TYPE: PRT
<213> ORGANISM: artificial
<220> FEATURE:
<223> OTHER INFORMATION: VIM-2 variant

<400> SEQUENCE: 16

Met Asp Ser Ser Gly Glu Tyr Pro Thr Ala Ser Glu Ile Pro Val Gly
1               5                   10                  15

Glu Val Arg Leu Tyr Gln Ile Ala Asp Gly Val Trp Ser His Ile Ala
            20                  25                  30

Thr Arg Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Asp Gly Leu Ser Ser Gly Asp Ala Val Arg Phe Gly Pro Val
    130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Thr Asn Val Val Lys Ala His Thr Asn Arg Ser Val Val Glu
225                 230                 235                 240

<210> SEQ ID NO 17
<211> LENGTH: 240
<212> TYPE: PRT
<213> ORGANISM: artificial
<220> FEATURE:
<223> OTHER INFORMATION: VIM-2 variant

<400> SEQUENCE: 17

Met Asp Ser Ser Gly Glu Tyr Pro Thr Ala Ser Glu Ile Pro Val Gly
1               5                   10                  15

Glu Val Arg Leu Tyr Asn Ile Ala Asp Gly Val Trp Ser His Ile Ala
            20                  25                  30

Thr Arg Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly

```
                85                  90                  95
Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
            115                 120                 125

Leu Asp Gly Leu Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
            165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
            195                 200                 205

Phe Val Ile Pro Gly His Gly Leu Pro Gly Gly Leu Asp Leu Leu Lys
            210                 215                 220

His Thr Thr Asn Val Val Lys Ala His Thr Asn Arg Ser Val Val Glu
225                 230                 235                 240

<210> SEQ ID NO 18
<211> LENGTH: 240
<212> TYPE: PRT
<213> ORGANISM: artificial
<220> FEATURE:
<223> OTHER INFORMATION: VIM-2 variant

<400> SEQUENCE: 18

Met Asp Ser Ser Gly Glu Tyr Pro Thr Ala Ser Glu Ile Pro Val Gly
1               5                   10                  15

Glu Val Arg Leu Tyr His Ile Ala Asp Gly Val Trp Ser His Ile Ala
            20                  25                  30

Thr Arg Ser Phe Asp Gly Ala Val Tyr Pro Ser Asn Gly Leu Ile Val
            35                  40                  45

Arg Asp Gly Asp Glu Leu Leu Leu Ile Asp Thr Ala Trp Gly Ala Lys
50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
            85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
            115                 120                 125

Leu Asp Gly Leu Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
            165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
            195                 200                 205

Phe Val Ile Pro Gly His Gly Leu Pro Gly Gly Leu Asp Leu Leu Lys
```

```
                    210                 215                 220
His Thr Thr Asn Val Val Lys Ala His Thr Asn Arg Ser Val Val Glu
225                 230                 235                 240

<210> SEQ ID NO 19
<211> LENGTH: 235
<212> TYPE: PRT
<213> ORGANISM: artificial
<220> FEATURE:
<223> OTHER INFORMATION: VIM-2 variant

<400> SEQUENCE: 19

Met Asp Ser Ser Gly Glu Tyr Pro Thr Ala Ser Glu Ile Pro Val Gly
1               5                   10                  15

Glu Val Arg Leu Tyr His Ile Ala Asp Gly Val Trp Ser His Ile Ala
                20                  25                  30

Thr Arg Ser Phe Asp Gly Ala Val Tyr Pro Ser Asn Gly Leu Ile Val
            35                  40                  45

Arg Asp Gly Asp Glu Leu Leu Leu Ile Asp Thr Ala Trp Gly Ala Lys
        50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Glu Gly Leu Ser Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
    210                 215                 220

His Thr Asn Val Val Lys Ala His Thr Asn
225                 230                 235

<210> SEQ ID NO 20
<211> LENGTH: 235
<212> TYPE: PRT
<213> ORGANISM: artificial
<220> FEATURE:
<223> OTHER INFORMATION: VIM-2 variant

<400> SEQUENCE: 20

Met Asp Ser Ser Gly Glu Tyr Pro Thr Ala Ser Glu Ile Pro Val Gly
1               5                   10                  15

Glu Val Arg Leu Tyr Asn Ile Ala Asp Gly Val Trp Ser His Ile Ala
                20                  25                  30

Thr Arg Ser Phe Asp Gly Ala Val Tyr Pro Ser Asn Gly Leu Ile Val
            35                  40                  45
```

```
Arg Asp Gly Asp Glu Leu Leu Leu Ile Asp Thr Ala Trp Gly Ala Lys
 50                  55                  60

Asn Thr Ala Ala Leu Leu Ala Glu Ile Glu Lys Gln Ile Gly Leu Pro
 65                  70                  75                  80

Val Thr Arg Ala Val Ser Thr His Phe His Asp Asp Arg Val Gly Gly
                 85                  90                  95

Val Asp Val Leu Arg Ala Ala Gly Val Ala Thr Tyr Ala Ser Pro Ser
                100                 105                 110

Thr Arg Arg Leu Ala Glu Val Glu Gly Asn Glu Ile Pro Thr His Ser
                115                 120                 125

Leu Glu Gly Leu Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
                180                 185                 190

Trp Pro Thr Ser Ile Glu Arg Ile Gln Gln His Tyr Pro Glu Ala Gln
                195                 200                 205

Phe Val Ile Pro Gly His Gly Leu Pro Gly Gly Leu Asp Leu Leu Lys
210                 215                 220

His Thr Thr Asn Val Val Lys Ala His Thr Asn
225                 230                 235

<210> SEQ ID NO 21
<211> LENGTH: 235
<212> TYPE: PRT
<213> ORGANISM: artificial
<220> FEATURE:
<223> OTHER INFORMATION: VIM-2 variant

<400> SEQUENCE: 21

Met Asp Ser Ser Gly Glu Tyr Pro Thr Ala Ser Glu Ile Pro Val Gly
 1               5                  10                  15

Glu Val Arg Leu Tyr Gln Ile Ala Asp Gly Val Trp Ser His Ile Ala
                 20                  25                  30

Thr Arg Ser Phe Asp Gly Ala Val Tyr Pro Ser Asn Gly Leu Ile Val
                 35                  40                  45

Arg Asp Gly Asp Glu Leu Leu Leu Ile Asp Thr Ala Trp Gly Ala Lys
 50                  55                  60

Asn Thr Ala Ala Leu Leu Ala Glu Ile Glu Lys Gln Ile Gly Leu Pro
 65                  70                  75                  80

Val Thr Arg Ala Val Ser Thr His Phe His Asp Asp Arg Val Gly Gly
                 85                  90                  95

Val Asp Val Leu Arg Ala Ala Gly Val Ala Thr Tyr Ala Ser Pro Ser
                100                 105                 110

Thr Arg Arg Leu Ala Glu Val Glu Gly Asn Glu Ile Pro Thr His Ser
                115                 120                 125

Leu Asp Gly Leu Ser Ser Gly Asp Ala Val Arg Phe Gly Pro Val
130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175
```

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
        210                 215                 220

His Thr Thr Asn Val Val Lys Ala His Thr Asn
225                 230                 235

<210> SEQ ID NO 22
<211> LENGTH: 235
<212> TYPE: PRT
<213> ORGANISM: artificial
<220> FEATURE:
<223> OTHER INFORMATION: VIM-2 variant

<400> SEQUENCE: 22

Met Asp Ser Ser Gly Glu Tyr Pro Thr Ala Ser Glu Ile Pro Val Gly
1               5                   10                  15

Glu Val Arg Leu Tyr Asn Ile Ala Asp Gly Val Trp Ser His Ile Ala
            20                  25                  30

Thr Arg Ser Phe Asp Gly Ala Val Tyr Pro Ser Asn Gly Leu Ile Val
        35                  40                  45

Arg Asp Gly Asp Glu Leu Leu Leu Ile Asp Thr Ala Trp Gly Ala Lys
    50                  55                  60

Asn Thr Ala Ala Leu Leu Ala Glu Ile Glu Lys Gln Ile Gly Leu Pro
65                  70                  75                  80

Val Thr Arg Ala Val Ser Thr His Phe His Asp Asp Arg Val Gly Gly
                85                  90                  95

Val Asp Val Leu Arg Ala Ala Gly Val Ala Thr Tyr Ala Ser Pro Ser
            100                 105                 110

Thr Arg Arg Leu Ala Glu Val Glu Gly Asn Glu Ile Pro Thr His Ser
        115                 120                 125

Leu Asp Gly Leu Ser Ser Ser Gly Asp Ala Val Arg Phe Gly Pro Val
    130                 135                 140

Glu Leu Phe Tyr Pro Gly Ala Ala His Ser Thr Asp Asn Leu Val Val
145                 150                 155                 160

Tyr Val Pro Ser Ala Ser Val Leu Tyr Gly Gly Cys Ala Ile Tyr Glu
                165                 170                 175

Leu Ser Arg Thr Ser Ala Gly Asn Val Ala Asp Ala Asp Leu Ala Glu
            180                 185                 190

Trp Pro Thr Ser Ile Glu Arg Ile Gln Gln His Tyr Pro Glu Ala Gln
        195                 200                 205

Phe Val Ile Pro Gly His Gly Leu Pro Gly Gly Leu Asp Leu Leu Lys
        210                 215                 220

His Thr Thr Asn Val Val Lys Ala His Thr Asn
225                 230                 235

<210> SEQ ID NO 23
<211> LENGTH: 235
<212> TYPE: PRT
<213> ORGANISM: artificial
<220> FEATURE:
<223> OTHER INFORMATION: VIM-2 variant

<400> SEQUENCE: 23

Met Asp Ser Ser Gly Glu Tyr Pro Thr Ala Ser Glu Ile Pro Val Gly
1               5                   10                  15

```
Glu Val Arg Leu Tyr His Ile Ala Asp Gly Val Trp Ser His Ile Ala
            20              25              30
Thr Arg Ser Phe Asp Gly Ala Val Tyr Pro Ser Asn Gly Leu Ile Val
        35              40              45
Arg Asp Gly Asp Glu Leu Leu Leu Ile Asp Thr Ala Trp Gly Ala Lys
    50              55              60
Asn Thr Ala Ala Leu Leu Ala Glu Ile Glu Lys Gln Ile Gly Leu Pro
65              70              75              80
Val Thr Arg Ala Val Ser Thr His Phe His Asp Asp Arg Val Gly Gly
            85              90              95
Val Asp Val Leu Arg Ala Ala Gly Val Ala Thr Tyr Ala Ser Pro Ser
        100             105             110
Thr Arg Arg Leu Ala Glu Val Glu Gly Asn Glu Ile Pro Thr His Ser
    115             120             125
Leu Asp Gly Leu Ser Ser Ser Gly Asp Ala Val Arg Phe Gly Pro Val
    130             135             140
Glu Leu Phe Tyr Pro Gly Ala Ala His Ser Thr Asp Asn Leu Val Val
145             150             155             160
Tyr Val Pro Ser Ala Ser Val Leu Tyr Gly Gly Cys Ala Ile Tyr Glu
            165             170             175
Leu Ser Arg Thr Ser Ala Gly Asn Val Ala Asp Ala Asp Leu Ala Glu
            180             185             190
Trp Pro Thr Ser Ile Glu Arg Ile Gln Gln His Tyr Pro Glu Ala Gln
        195             200             205
Phe Val Ile Pro Gly His Gly Leu Pro Gly Gly Leu Asp Leu Leu Lys
        210             215             220
His Thr Thr Asn Val Val Lys Ala His Thr Asn
225             230             235
```